US006545183B1

(12) United States Patent
Berens

(10) Patent No.: US 6,545,183 B1
(45) Date of Patent: *Apr. 8, 2003

(54) PROCESS FOR PREPARING CYCLIC PHOSPHINES

(75) Inventor: Ulrich Berens, Grenzach-Wyhlen (DE)

(73) Assignee: Chirotech Technology Limited, Cambridge (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/530,845

(22) PCT Filed: May 11, 1998

(86) PCT No.: PCT/GB98/03321

§ 371 (c)(1),
(2), (4) Date: Jul. 6, 2000

(87) PCT Pub. No.: WO99/24444

PCT Pub. Date: May 20, 1999

Related U.S. Application Data

(60) Provisional application No. 60/068,675, filed on Dec. 24, 1997.

(30) Foreign Application Priority Data

Nov. 7, 1997 (GB) .............................................. 9723583

(51) Int. Cl.[7] .................................................. C07F 9/50
(52) U.S. Cl. ....................................................... 568/12
(58) Field of Search ....................... 568/12, 8; 556/140, 556/13, 20

(56) References Cited

U.S. PATENT DOCUMENTS

| 5,399,771 A | | 3/1995 | Cai et al. | |
| 5,532,395 A | * | 7/1996 | Burk | ............................ 556/18 |
| 5,936,109 A | * | 8/1999 | Berens | ......................... 556/14 |

FOREIGN PATENT DOCUMENTS

| GB | 2262284 | 6/1993 |
| WO | 9301199 | 1/1993 |
| WO | 9802445 | 1/1998 |

OTHER PUBLICATIONS

CA:117:193982 abs of Neftekhimiya by Arshinova et al 32(3) pp 235–242, 1992.*
CA:83:206378 abs of Zh. Obshch. Khim. by Azerbaev et al 45(8) pp 1730–1734, 1975.*
Wilson, Stephen R. et al. (1990) "Preparation of a New Class of C2–Symmetric Chiral Phosphines: The First Asymmetric Staudinger Reaction" 6139 Synlett, No. 4, Stuttgart, DE, pp. 199–200.

* cited by examiner

Primary Examiner—Jean F. Vollano

(57) ABSTRACT

The present invention concerns the preparation of a cyclic phosphine from the corresponding primary phosphine and a bifunctional alkylating agent, wherein alkylation, and displacement of each functional group, occurs in the presence of a strong base, is modified by adding the strong base, in an amount sufficient for cyclisation, to a preformed mixture or reaction product of the primary phosphine and the alkylating agent.

17 Claims, No Drawings

PROCESS FOR PREPARING CYCLIC PHOSPHINES

CROSS-REFERENCE TO RELATED APPLICATIONS

This application is a 371 of PCT/GB98/03321, filed Nov. 5, 1998, now WO 99/24444.

This application claims the benefit of U.S. Provisional Application No. 60/068,675, filed Dec. 24, 1997.

FIELD OF THE INVENTION

This invention relates to processes suitable for the large-scale preparation of enantiomerically-enriched cyclic phosphines, especially those useful as ligands in asymmetric hydrogenation catalysts.

BACKGROUND OF THE INFVENTION

Chiral cyclic phosphines are useful ligands for asymmetric catalysis. In particular, chiral ligands of the DuPHOS and BPE series, respectively represented by formulae (1) and (2)

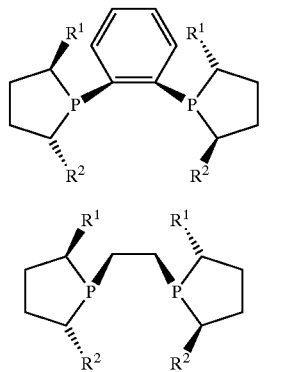

wherein $R^1$ and $R^2$ are typically $C_{1-6}$ linear or branched alkyl, and enantiomeric forms thereof, can be used to prepare rhodium and ruthenium complexes, which are effective and versatile catalysts for asymmetric hydrogenation of a diverse range of substrate types. For a review, see Burk et al, Pure Appl. Chem. (1996) 68:37–44.

Such catalysts are eminently suitable for industrial applications, especially for the provision of chiral pharmaceutical intermediates in high enantiomeric purity. For this purpose, and in other industrial applications such as flavour and fragrance fine chemicals, the development of manufacturing processes requires in turn large amounts of a ligand (1) or (2), e.g. in kilogram quantity or greater. Thus, there is a requirement for efficient and scaleable methods for synthesis of such ligands.

As described in U.S. Pat. No. 5,532,395 and WO 93/01199, an established procedure for the preparation of DuPHOS and BPE ligands entails the reaction of a bis(primary)phosphine with a 1,4-alkanediol cyclic sulphate mediated by a strong base capable of deprotonating a P—H bond, typically n-butyllithium. 2 Equivalents of the cyclic sulphate, optionally in a small excess, and at least 4 equivalents of base are required. A representative process of this type, for the preparation of (S,S)-methyl DuPHOS, is shown in the following scheme:

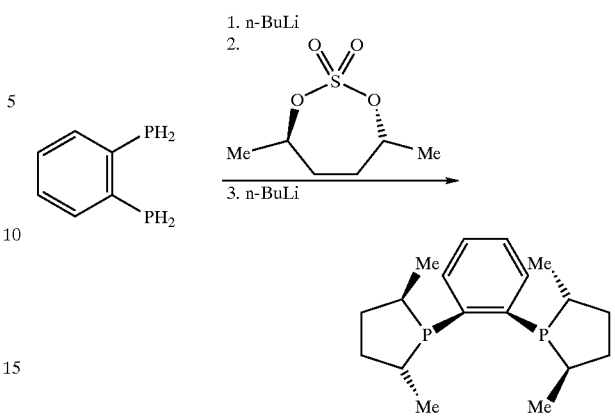

The literature procedure stipulates that reactants should be added to the reaction vessel in the following order:

(a) 2 equivalents of n-butyllithium are added to a solution of 1,2-bis(phosphino)benzene in THF at 20–30° C., ostensibly to generate dilithium 1,2-bis(phosphido) benzene;

(b) after 1–1.5 h, a solution of (R,R)-1,4-hexanediol cyclic sulphate (2 equivalents) in THF is added to the resultant mixture;

(c) after a further 1 h, a second aliquot of n-butyllithium (2.2–2.3 equivalents) is added;

(d) at the end of the reaction, work-up comprises addition of methanol and successive cycles of filtration, solvent washing and solvent evaporation, with progressive reduction in solvent polarity (diethyl ether, then pentane). An aqueous work-up is avoided.

The protocol described above is well suited to laboratory-scale synthesis of a ligand of formula (1) or (2), typically to prepare 1–10 g quantities. At this scale, operating parameters such as temperature, reaction duration, request stoichiometry, and exclusion of air and moisture are easily controlled. However, on a larger scale, it has been found that it is more difficult to achieve the same yield of the ligand, and that side-reactions can hinder ligand purification. This may be a consequence of one or more factors, such as inadequate exclusion of air and moisture in a manufacturing plant vessel, and, in order to maintain temperature control, prolonged duration of reagent addition and overall reaction time. Without wishing to be bound by theory, anionic species generated in step (a) have a longer residence time, and may be consumed by reaction with the solvent (TBF). Thus yields in steps (b) and (c) are reduced.

For example, U.S. Pat. No. 5,532,395 describes the preparation of (S,S)-methyl DUPHOS from 0.8 g of 1,2-bis(phosphino)benzene, in which a yield of 78% is achieved. In contrast, when scaling up this procedure by a factor of 75, using 60 g of 1,2-bis(phosphino)benzene, the yield of methyl DuPHOS can fall to below 30%. Overall, such lowering of yield has an adverse effect on the economics of the process.

Wilson and Pasternak, Synlett 4:199–200 (April 1990), discloses the preparation of chiral phosphines for use in an asymmetric Staudinger reaction.

U.S. Pat. No. 5,399,771 discloses the preparation of BINAP using diphenylphosphine, an amine base and a nickel catalyst.

GB-A-2262284 discloses the preparation of tertiary phosphines.

SUMMARY OF THE INVENTION

This invention is based on the discovery that an efficient, high-yielding preparation of a cyclic phosphine is facilitated by a new mode of reagent addition. More specifically, a process for the preparation of a cyclic phosphine from the corresponding primary phosphine and a bifunctional alkylating agent, wherein alkylation, and displacement of each functional group, occurs in the presence of a strong base, comprises adding the strong base, in an amount sufficient for cyclisation, to a preformed mixture or reaction product of the primary phosphine and alkylating agent.

It is surprising that high yields are achieved in this process, given the potential for side-reactions, which an individual of ordinary skill in the art might predict. In particular, the bifunctional alkylating agent is susceptible to β-elimination by reaction with a strong base. However, in practice, β-elimination is not observed as a major reaction pathway. Also noteworthy is the fact that this process allows the preparation of phosphines bearing very hindered functional groups such as tert-butyl through substitution at neopentyl-like centres of the alkylating agent.

In addition to improvements in yield and product purity, simplicity of process operation is another benefit when compared to the original protocol, since all of the base required to mediate the reaction is added in a single operation, after the reaction vessel has been charged with all other reactants. Moreover, it is found that, in general, cyclic phosphines withstand aqueous work-up, which is advantageous in terms of material transfer/handling, allowing convenient separation of ionic species (salts, etc) from the product.

DESCRIPTION OF THE INVENTION

The process of this invention preferably comprises the addition of at least 2 m equivalents of a strong base to a mixture or reaction product of the primary phosphine and at least m equivalents of the bifunctional alkylating agent. The cyclic phosphine, the primary phosphine and the bifunctional alkylating agent that are used in this invention are preferably respectively of formula (3), (4) and (5)

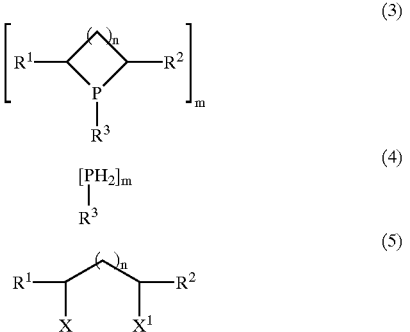

In formulae (3)–(5), $R^1$ and $R^2$ are independently H, alkyl, cycloalkyl, aryl, aralkyl or alkaryl, provided that both are not H, $R^3$ is aryl, alkyl, cycloalkyl, aralkyl, alkaryl, or an organometallic residue such as ferrocenyl; m is 1 or 2; n is in the range 1–4; and X and $X^1$ are the same or different nucleofugal leaving groups, optionally linked to form a ring. The cyclic phosphine ring in (3) may optionally form part of a fused polycyclic ring system.

Any base capable of effecting complete deprotonation of a P—H bond is suitable for use in the novel process. Commercially available organolithium bases are ideal for this purpose and alkyllithiums are preferred, especially n-butyllithium and sec-butyllithium. A variety of solvents may be used, particularly ethereal solvents such as tetrahydrofuiran (TBF), diglyme, diethyl ether or t-butyl methyl ether. THF is the preferred solvent, and hydrocarbon solvents, e.g. hexanes, such as might be used for dissolution of an organolithium base, are compatible as cosolvents.

A preferred embodiment of the present invention is a process for preparation of enantiomerically-enriched ligands of formula (3), from enantimerically-enriched alkylating agents of formula (5). The degree of enrichment is typically at least 70% ee, preferably at least 80% ee, more preferably at least 90% ee, and most preferably at least 95% ee.

Further, it is preferred that $R^1$ and $R^2$ are orientated trans to one another. Usually, although not necessarily, $R^1$ and $R^2$ are the same. This encompasses ligands of the DuPHOS (1) and BPE (2) series and monophosphospholane variants thereof. Further, it includes the use of phosphetane ligands, as disclosed in WO 98/02445, of formula (6)

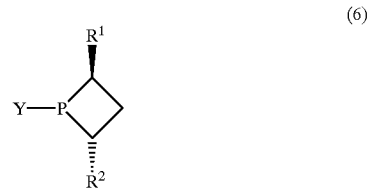

For monophosphetanes (6) wherein Y=Ph, the process of the present invention is especially advantageous, since transfer of a solution of lithiated phenylphosphine between reaction vessels is avoided, thereby reducing the exposure risk to this noxious and foul-smelling substance.

In another embodiment of the present invention, the preparation of novel ferrocenyl bisphosphetanes of formula (7)

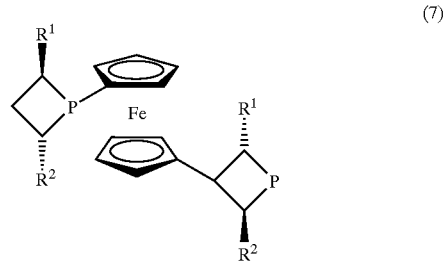

and opposite enantiomers thereof, wherein $R^1$ and $R^2$ are linear or branched alkyl, demonstrates functional group compatibility. In the case of compounds of formula (7) wherein $R^1=R^2=$t-Bu, controlled nucleophilic substitution at neopentyl-like centres may be achieved.

For preparation of ligands of formulae (1), (2), (6) and (7), and related compounds, preferred bifunctional alkylating agents are those prepared from the corresponding single enantiomer 1,3- and 1,4-diols. Cyclic sulphate derivatives are preferred, although bis(aryl)sulphonates or bis(alkyl) sulphonates, such as ditosylates, can be used with equal facility. 1,4-Diol precursors of phospholane ligands (1) and (2) can be prepared either by electrochemical Kolbe coupling [see Burk et al, Organometallics (1990) 9:2653] or more conveniently via biocatalytic resolution of racemic diols [Berens, Proceedings of Chiral Europe 1996 (Spring Innovations Ltd.), p. 13]. 1,3-Diol precursors of phosphetanes (6) are easily accessible by asymmetric hydrogenation of the corresponding 1,3-diketones (for lead references, see WO 98/02445).

The following Examples illustrate the invention.

EXAMPLE 1

1,2-bis((2R,5R)2,5-Dimethylphospholano)benzene (R,R)MeDuPHOS

A solution of n-BuLi in hexanes (2.958 mol; 1.183 L of 2.5 N solution), diluted with diethyl ether (2.5 L), was added over 4 hours to a stirred mixture of 1,2-bis(phosphino) benzene (100 g, 0.7042 mol) and the cyclic sulfate (4R,7R) 4,7-dimethyl-2,2-dioxo-1,3,2-dioxathiepane (266.5 g, 1.479 mol, 5% excess) in TIF (8 L), under a nitrogen atmosphere, whilst maintaining an internal temperature of 10–15° C. After the BuLi-solution had been added completely, the mixture was stirred for another 10 minutes, and then quenched by the addition of water (ca. 20 mL). The solvent was evaporated on a rotavapor, and to the residue was added water (ca. 1 L) to dissolve the lithium sulfate. The pH was adjusted to 3 by the addition of diluted (2 N) sulfuric acid. The ligand was extracted from this mixture with tert-butyl methyl ether (1×1 L, 3×500 ml). After drying and removal of the solvent, methanol (ca. 500 mL) was added carefully to the crude ligand to induce crystallisation. After standing overnight in the refrigerator, the crystals were filtered off and dried in vacuum. Evaporating the solvent from the filtrate and recrystallisation of the residue from little MeOH yielded another crop of Me-DuPHOS. White crystals, mp.=80–81° C.; combined yield 151 g (70.0% based on 1,2-bis-(diphosphino)benzene).

EXAMPLE 2

(2S,5S)-2,5Dimethyl-1-(naphth-1-yl)phospholane

A solution of n-BuLi in hexanes (21 mmol; 8.4 ml of 2.5 N solution), diluted with diethyl ether (20 mL), was added over 30 minutes to a stirred mixture of 1-naphthylphosphine (1.6 g, 10 mmol) and the cyclic sulfate (4R,7R)4,7-dimethyl-2,2-dioxo-1,3,2-dioaxathiepane (1.89 g, 10.5 mmol, 5% excess) in THF (100 ml), under a nitrogen atmosphere. After the complete addition of BuLi, the deep orange mixture was stirred for another 10 minutes, and then quenched by the addition of MeOH (2 ml). Then the solvent was removed on the rotavapor, and to the residue was added water. The product was extracted with pentane (3×50 ml) and, after drying the combined organic layers and removal of the solvent, the essentially pure phosphine was obtained as an oil. Yield 1.73 g (71.1% based on naphthylphosphine). $^{31}$P-NMR (CDCl$_3$, 400 MHz): d=–6.00 ppm.

EXAMPLE 3

Cis- and Trans-meso-2,5-Dimethyl-1-phenylphospholane

A solution of n-BuLi in hexanes (21 mmol; 8.4 ml of 2.5 N solution), diluted with diethyl ether (20 ml), was added over 30 minutes to a stirred mixture of phenylphosphine (1.1 g, 10 mmol) and meso-2,5-di-O-tosyl-hexane (4.48 g, 10.5 mmol, 5% excess) in THF (150 ml), under a nitrogen atmosphere. After the complete addition of the BuLi, the solvent, was removed from the reaction mixture on the rotavapor. To the residue was added water, and the product was extracted with pentane in three portions (50 ml each). After drying the combined organic layers and removal of the solvent, the product was obtained as an oil. Yield 1.72 g (89.5% based on phenylphosphine) of a 88:12 mixture of trans- and cis-meso-2,5-direthyl-1-phenyl-phospholane.

EXAMPLE 4

(2R,4R)-2,4-Diethyl-1-phenylphosphetane

A solution of n-BuLi in hexanes (88 ml of 2.5 N solution), diluted with diethyl ether (400 ml), was added over 3 hours to a stirred mixture of phenylphosphine (10.0 g, 90.1 mmol) and the cyclic sulfate (4S,7S)-4,7-diethyl-2,2-dioxo-1,3,2-dioxathian (19.6 g, 0.1 mol, 10% excess) in of THF (1 L), under a nitrogen atmosphere. The mixture was maintained at a temperature of –30° C. during the first half of the addition period, with cooling to –75° C. for the second half. The mixture was then left to warm overnight. After removal of the solvent, pentane (250 ml) and water (100 ml) were added to the residue. The organic layer was dried, and the solvent was removed to leave the phosphetane as a pale yellow oil which was pure with the exception of a small amount of unreacted phenylphosphine as impurity. After distillation (bp.=81° C. at 0.05 mm), 9.94 g of (2R,4R)-2,4-diethyl-1-phenylphosphetane (53% yield based on phenylphosphine) was obtained.

EXAMPLE 5

1,2-Bis((2S,5S)-2,5diethylphospholano)ethane (S,S) Et-BPE 1,2-Bis(phosphino)ethane (12.0 g, 0.1276 mol) was added to a solution of the cyclic sulfate (4R,7R)-4,7-diethyl-2,2-dioxo-1,3,2-dioaxathiepane (55.9 g, 0.2683 mol, 5% excess) in 1 L of THF, under nitrogen. A solution of 2.5 N n-BuLi (211.3 ml, 0.528 mol) in ether (300 ml), was added under rapid stirring within 120 minutes, while the internal temperature was maintained at 10° C. by cooling with an ice bath. After the complete addition of the BuLi there was no colour, thus more BuLi (ca. 10 ml) was added, until the colour was yellow. The mixture was then quenched by the addition of MeOH (5 ml), and the solvent was removed on the rotavapor. To the residue was added water (150 ml), and the product was extracted with pentane (3×80 ml). After drying of the combined organic layers (Na$_2$SO$_4$) and removal of the solvent, the essentially pure phosphine was obtained as an oil. Distillation over a 30 cm Vigreux column gave a fraction boiling from 140 to 143° C. at 0.02 mm, which contained 34.02 g of pure ligand (84.8% based on 1,2-bis(phosphino)ethane).

EXAMPLE 6

1,1'-bis((2S,4S)-2,4-diisopropylphosphetan-1-yl) ferrocene

A solution of the cyclic sulfate (4R,6R)-4,6-diisopropyl-2,2-dioxo-1,3,2-dioxathiolane (3.7 g, 16.8 mmol, 5% excess) in 200 mL of THF in a 500 mL flask was sparged with nitrogen for 45 minutes. A dropping funnel which was attached to the middle neck of the flask was charged with a solution of 1.3 N sec-BuLi (31.0 ml, 40.3 mmol) in pentanes (100 mL). Under exclusion of air, 1,1'-bis(phosphino) ferrocene (2.0 g, 8 mmol) was added via syringe to the solution of the cyclic sulfate (no stirring), and then the solution of sec-BuLi was added at 0° C. under rapid stirring within one hour. When the addition of the sec-BuLi was complete, the mixture was stirred for another 2 minutes and then the excess base was quenched by the addition of 2 mL of MeOH. The solvent was then removed on the rotavapor, and the residue was dissolved in water/saturated NH$_4$Cl (100/50 mL). This mixture was extracted twice with petrol ether (bp. 40–60° C., 100 and 50 mL). The combined organic layer was dried (Na$_2$SO$_4$), and removal of the solvent gave 3.99 g of a crystalline material. This was redissolved in ca. 5 mL of petrol ether, and after the addition of ca. 20 mL of methanol, the product crystallised. Fine yellow needles, 2.85 g, 71.5% yield, mp=115–116° C. by DSC.

EXAMPLE 7

1,1'-bis((2S,4S)-2,4-di-tert-butylphosphetan-1-yl) ferrocene

A solution of the cyclic sulfate (4R,6R)-4,6-di-4-butyl-2,2-dioxo-1,3,2-dioxathiolane (4.2 g, 16.8 mmol, 5% excess) in 300 mL of THF in a 500 mL flask was sparged with nitrogen for 45 minutes. A dropping funnel which was attached to the middle neck of the flask was charged with a solution of 1.3 N sec-BuLi (27.1 ml, 35.2 mmol) in pentanes (50 mL). Under exclusion of air, 1,1'-bis(phosphino)ferrocene (2.0 g, 8 mmol) was added via syringe to the solution of the cyclic sulfate (no stirring), and then the solution of sec-BuLi was added at 0° C. under rapid stirring within one hour. After the complete addition of the sec-BuLi the mixture was stirred for another 10 minutes and then the excess base was quenched by the addition of methanol. The solvent was then removed on the rotavapor, and the residue was distributed between water/pentane (100 and 2×50 mL of pentane). The combined organic layer was dried (Na$_2$SO$_4$), and removal of the solvent gave 3.4 g of a bright yellow-orange solid. The material was recrystallised from methanol (ca. 50 mL) and gave, after two recrystallisations, 1.12 g (25%) of the product.

What is claimed is:

1. A process for the preparation of a cyclic phosphine from the corresponding primary phosphine and a bifunctional alkylating agent, wherein alkylation, and displacement of each functional group, occurs in the presence of a strong base, which comprises adding the strong base, in an amount sufficient for cyclisation, to a preformed mixture or reaction product of the primary phosphine and the bifunctional alkylating agent, wherein the cyclic phosphine is of formula (3), the primary phosphine is of formula (4) and the bifunctional alkylating agent is of formula (5)

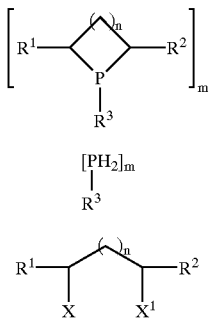

wherein m and n are positive integers, the groups R$^1$, R$^2$ and R$^3$ are each any non-interfering radical, wherein R$^1$ and R$^2$ are independently H, alkyl cycloalkyl aryl, aralkyl or alkaryl, provided that both are not H, and R$^3$ is aryl, alkyl, cycloalkyl, aralkyl, alkaryl or an organometallic residue, and wherein X and X$^1$ are each nucleofugal leaving groups, optionally linked to form a ring.

2. The process according to claim 1, which comprises the addition of the strong base to a mixture or reaction product of the primary phosphine of formula (4) and the bifunctional alkylating agent of formula (5), wherein the ratio of the strong base and the bifunctional alkylating agent is 2:1 equivalents, respectively.

3. The process according to claim 1, for the preparation of an enantiomerically-enriched cyclic phosphine of formula (3) from an enantiomerically-enriched bifunctional alkylating agent of formula (5).

4. The process according to claim 1, wherein the orientation of R$^1$ and R$^2$ in the cyclic phosphine of formula (3) is trans.

5. The process according to claim 1, wherein m is 1 or 2; n is an integer of 1–4; and wherein the cyclic phosphine ring in formula (3) optionally forms part of a fused polycyclic ring system.

6. The process according to claim 5, wherein R$^1$=R$^2$ and n is 1 or 2.

7. The process according to claim 6, wherein n is 2.

8. The process according to claim 7, wherein m is 2.

9. The process according to claim 8, wherein the primary phosphine of formula (4) is 1,2-bis(phosphino)benzene or 1,2-bis(phosphino)ethane, for the preparation of a cyclic diphosphine of formula (1) or (2)

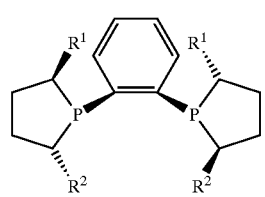

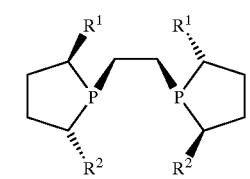

or the opposite enantiomer thereof, wherein R$^1$=R$^2$=linear or branched C$_{1-6}$ alkyl.

10. The process according to claim 7, wherein m is 1 and R$^3$ is aryl.

11. The process according to claim 6, wherein n is 1.

12. The process according to claim 11, wherein m is 2.

13. The process according to claim 12, wherein R$^3$ is ferrocenyl.

14. The process according to claim 11, wherein m is 1 and R$^3$ is aryl.

15. The process according to claim 1, wherein X and X$^1$ are linked to form a ring and the bifunctional alkylating agent of formula (5) is a cyclic sulphate.

16. The process according to claim 1, wherein the base is an alkyl or aryl lithium.

17. The process according to claim 16, wherein the base is n-butyllithium or sec-butyllithium.

* * * * *